(12) United States Patent
Chen

(10) Patent No.: US 8,097,215 B2
(45) Date of Patent: Jan. 17, 2012

(54) WALL-MOUNTED AROMATIC AIR FRESHENER DEVICE

(76) Inventor: Hui-Chin Chen, Shanghai (CN)

( * ) Notice: Subject to any disclaimer, the term of this patent is extended or adjusted under 35 U.S.C. 154(b) by 299 days.

(21) Appl. No.: 12/581,127

(22) Filed: Oct. 17, 2009

(65) Prior Publication Data
US 2011/0091358 A1  Apr. 21, 2011

(51) Int. Cl.
*A62B 7/08* (2006.01)
*A61L 9/00* (2006.01)
(52) U.S. Cl. ............. 422/123; 422/120; 422/122; 422/5
(58) Field of Classification Search .................. 422/120, 422/123, 5, 122; 220/477, 478
See application file for complete search history.

(56) References Cited

U.S. PATENT DOCUMENTS

| | | | |
|---|---|---|---|
| 5,735,918 A * | 4/1998 | Barradas | ......................... 96/222 |
| 6,123,935 A * | 9/2000 | Wefler et al. | ................. 424/76.1 |
| 6,779,905 B1 * | 8/2004 | Mazursky et al. | ............ 362/101 |
| 2004/0247300 A1 * | 12/2004 | He et al. | ........................ 392/390 |
| 2006/0196965 A1 * | 9/2006 | Christianson et al. | .......... 239/60 |
| 2007/0076440 A1 * | 4/2007 | Chien | ........................... 362/643 |
| 2007/0243791 A1 * | 10/2007 | Stedman | ...................... 446/227 |
| 2009/0134239 A1 * | 5/2009 | Neumann | ....................... 239/57 |

* cited by examiner

*Primary Examiner* — Sean E Conley
*Assistant Examiner* — Regina M. Yoo
(74) *Attorney, Agent, or Firm* — Wang Law Firm, Inc.; Li K. Wang

(57) ABSTRACT

A wall-mounted aromatic air freshener device includes a board, and a housing and a frame, both disposed at a backside of the board, a container disposed in the housing for containing an essential oil, a light emitting element and a light emitting control element, both installed in the frame, a switch device for turning on or off the light emitting element, such that an oil wick can absorb and vaporize an essential oil to disperse an aromatic air, and the light emitting element produces an optical decorative effect, so as to constitute the aromatic air freshener device.

7 Claims, 7 Drawing Sheets

WALL-MOUNTED AROMATIC AIR FRESHENER DEVICE

BACKGROUND OF THE INVENTION

1. Field of the Invention

The present invention relates to a wall-mounted aromatic air freshener device, and more particularly to an aromatic air freshener device mounted on a wall for producing aromatic air and providing an optical decorative effect.

2. Description of the Related Art

At present, air freshener products for dispersing aromatic air available in the market are mainly divided into the following three types:

1. The first type includes scented candles, potpourri pots, and any other products that disperse aromatic air by burning the products and produce an optical decorative effect by a fire source.

2. The second type includes electric insetting products that convert electric energy into heat energy to disperse aromatic air from an aromatic substance. Compared with the first type, the second type has a better effect of dispersing aromatic air.

3. The third type includes products that disperse aromatic air by a capillary action of an aromatic substance. This type of products is generally designed with a decorative appearance and disperses a mild aromatic odor.

However, the aforementioned first and second types of air freshener products require heat energy to produce aromatic air. Regardless of direct burning or energy conversion, practical applications may cause a fire accident. For example, the first type of products may be burned by accident if these products are placed near a fire source, and the second type of products may cause an electric fire. Although the third type of aromatic air freshener products can disperse aromatic air, yet the optical decorative effect of this type is incomparable to the first and second types.

Therefore, it is a key point of the present invention to overcome the aforementioned drawbacks of the prior art.

SUMMARY OF THE INVENTION

Therefore, it is a primary objective of the present invention to overcome the aforementioned shortcoming and deficiency of the prior art by providing a wall-mounted aromatic air freshener device for dispersing an aromatic air from the board and providing an amazing optical decorative effect by the light emitting element, after the air freshener device is mounted onto a wall.

To achieve the foregoing objective, the present invention provides an aromatic air freshener device, comprising:

a board, capable of absorbing and vaporizing an essential oil, and having a decorative surface formed on a front side of the board, and two protrusions disposed on a back side of the board;

a housing, having two grooves disposed inwardly from a backside of the housing, a hook portion mounted onto a wall, such that the housing is fixed by sheathing the two protrusions into the two grooves respectively, a space formed in the housing for accommodating a container filled with an aromatic essential oil, a cover covered onto this space, a clamp portion disposed in the space of the housing for clamping anterior end of the container, a prop portion disposed at the bottom of the cover and in a covering direction for propping the essential oil container into an oblique surface, an insert slot for receiving the prop portion when the cover is covered onto the space of the housing, and an oil wick extended from the interior of the container to an anterior end of the container for absorbing the essential oil, and contacting one of the two protrusions when the container is propped, such that the essential oil in the container is absorbed by the board; and a frame, installed around an external periphery of the housing, and having at least one light emitting element installed at a side of the frame, a reflective plate installed to a side of the light emitting element for increasing a light emitting area and a switch device for turning on or off the light emitting element.

The foregoing and other objectives and advantages of the present invention will become apparent with the following detailed description of preferred embodiments and related drawings.

Of course, another element and/or an arrangement of elements of the present invention may be altered or modified in an equivalent manner, and the invention is not limited to the preferred embodiments and drawings used in this specification only.

DETAILED DESCRIPTION OF THE PREFERRED EMBODIMENTS

Figure 1:
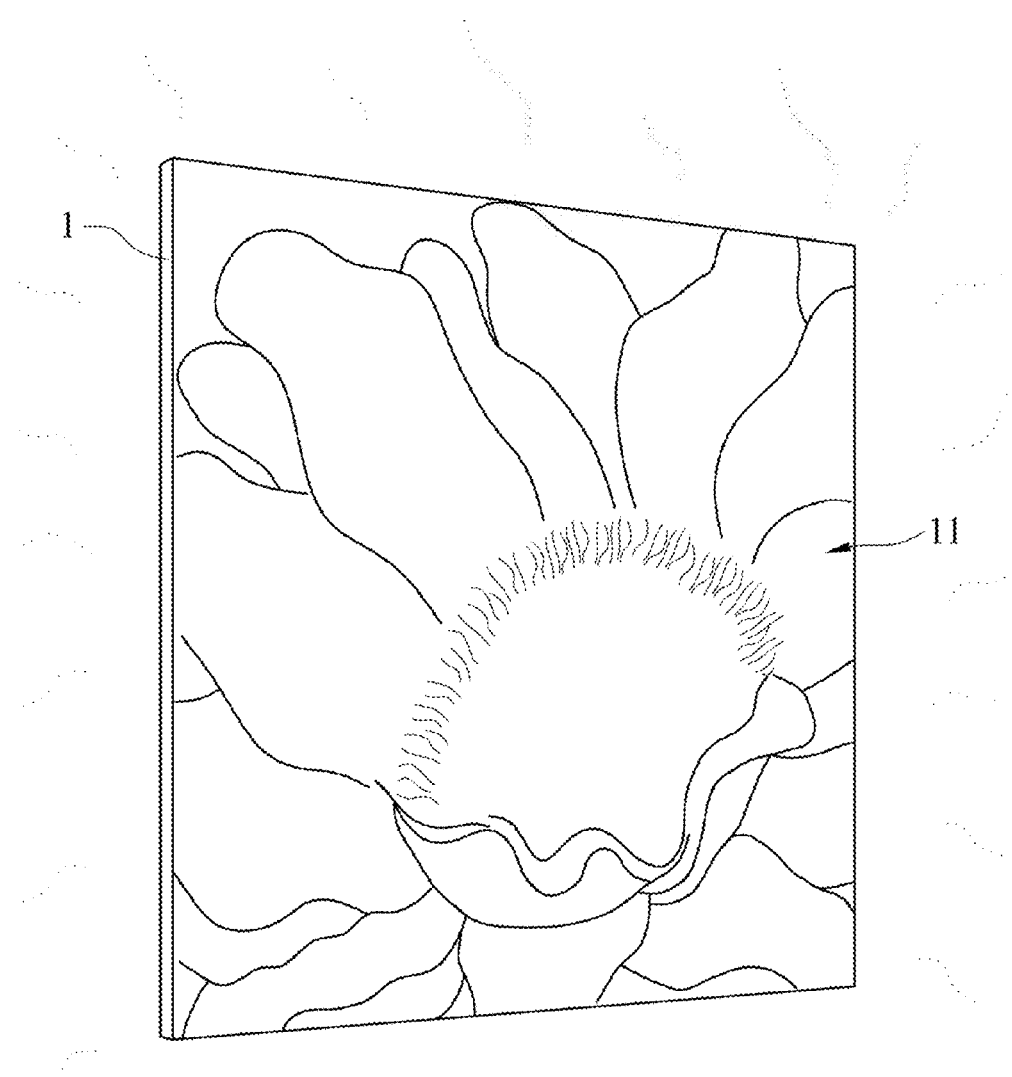
FIG. 1 is a perspective front view of the present invention.

With reference to FIGS. 1 to 7 for an aromatic air freshener device in accordance with a of the present invention, this preferred embodiment is provided for the purpose of illustrating the present invention only, but not intended for limiting the scope of the invention.

In this preferred embodiment, a wall-mounted aromatic air freshener device comprises the following elements:

A board 1 is capable of absorbing and vaporizing an essential oil, and includes a decorative surface 11 disposed at a front side of the board 1, and two protrusions 12, 13 disposed on a backside of the board 1, wherein the decorative surface 11 has a flower pattern, and the protrusion 12 is disposed at the top of the backside of the board 1, and the protrusion 13 is disposed at the bottom of the backside of the board 1, and the protrusion 12 includes two through holes 121, and a recession 122 disposed on a backside of the protrusion 12.

Figure 3:
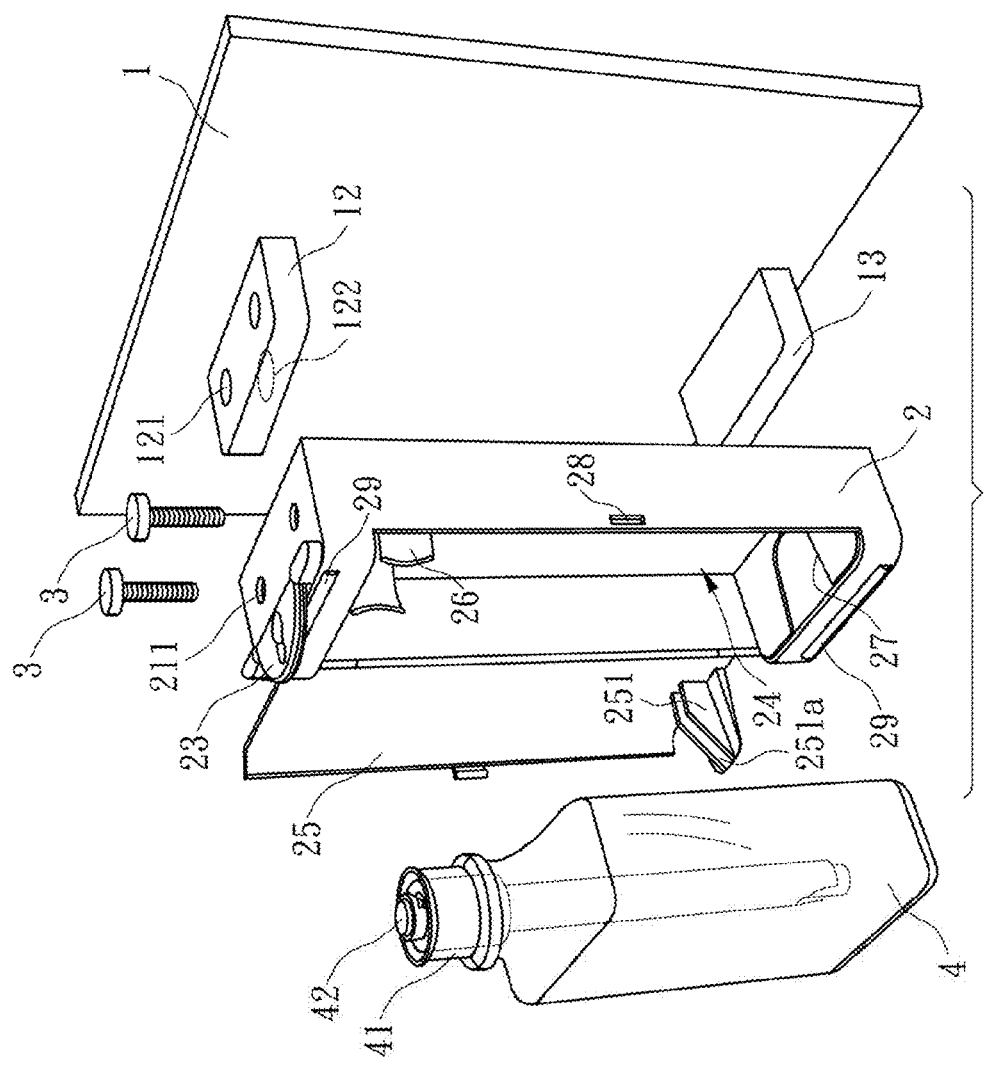
FIG. 3 is a perspective exploded view of the present invention.
Figure 4:
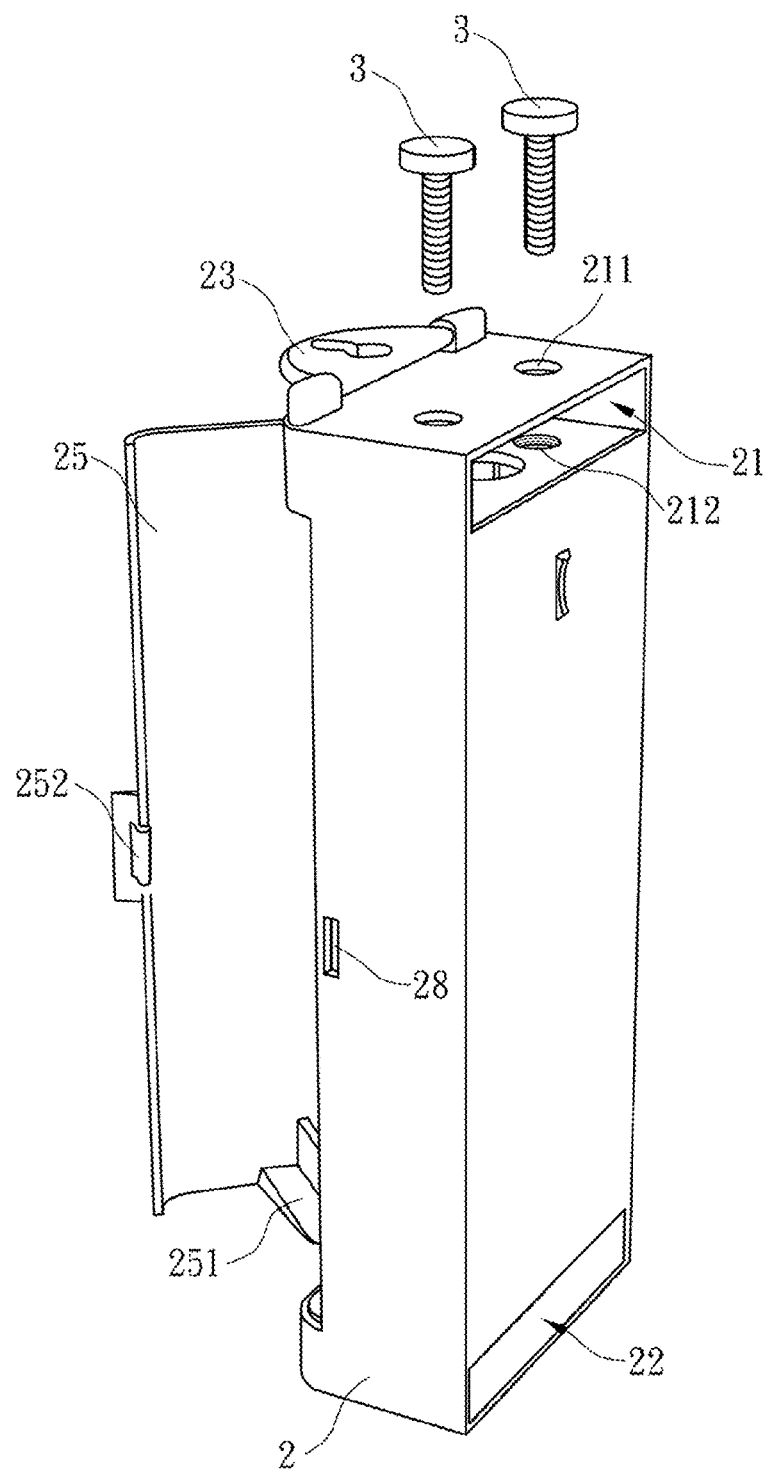
FIG. 4 is a perspective view of a backside of a housing of the present invention.

A housing 2 as shown in FIGS. 3 and 4 includes two grooves 21, 22 disposed inwardly on the backside of the housing 2, and a hook portion 23 for mounting the housing 2 on a wall, such that the housing 2 can be fixed by sheathing the two protrusions 12, 13 into the two grooves 21, 22 respectively. In this preferred embodiment, the housing 2 includes the two grooves disposed at top and bottom of a backside of the housing 2 and corresponding to the two protrusions respectively, two through holes 211 disposed at the top of the housing 2 and penetrated into the top of the groove 21, a screw hole 212 formed at the bottom inside the groove 21 of the housing 2 and corresponding to the two through holes 211, such that after the two protrusions 12, 13 are sheathed into the two grooves 21, 22 respectively by passing two bolts 3 into the through holes 211, 121, the two protrusions 12, 13 are secured into the screw hole 212 for fixing the housing 2 onto the board 1.

In FIG. 3, the housing 2 includes a space 24 disposed therein for accommodating the container 4 filled with an aromatic essential oil, and a cover 25 is covered onto the space 24, and the housing 2 further includes a clamp portion 26 inside the space 24 for clamping the anterior end 41 of the container 4. The cover 25 includes a prop portion 251 at the bottom of the cover 25 and towards a covering direction, and the cover 25 makes use of an oblique surface 251a of this prop portion 251 to prop the container 4, and the housing 2 has an insert slot 27 in the space 24 for receiving the prop portion 251 when the cover 25 is covered onto the housing 1, wherein the cover 25 includes a latch 252 disposed thereon, and the housing 2 includes a latch slot 28, such that when the cover 25 is covered onto the housing 2, the latch 52 is latched and fixed to the latch slot 28.

Figure 5:
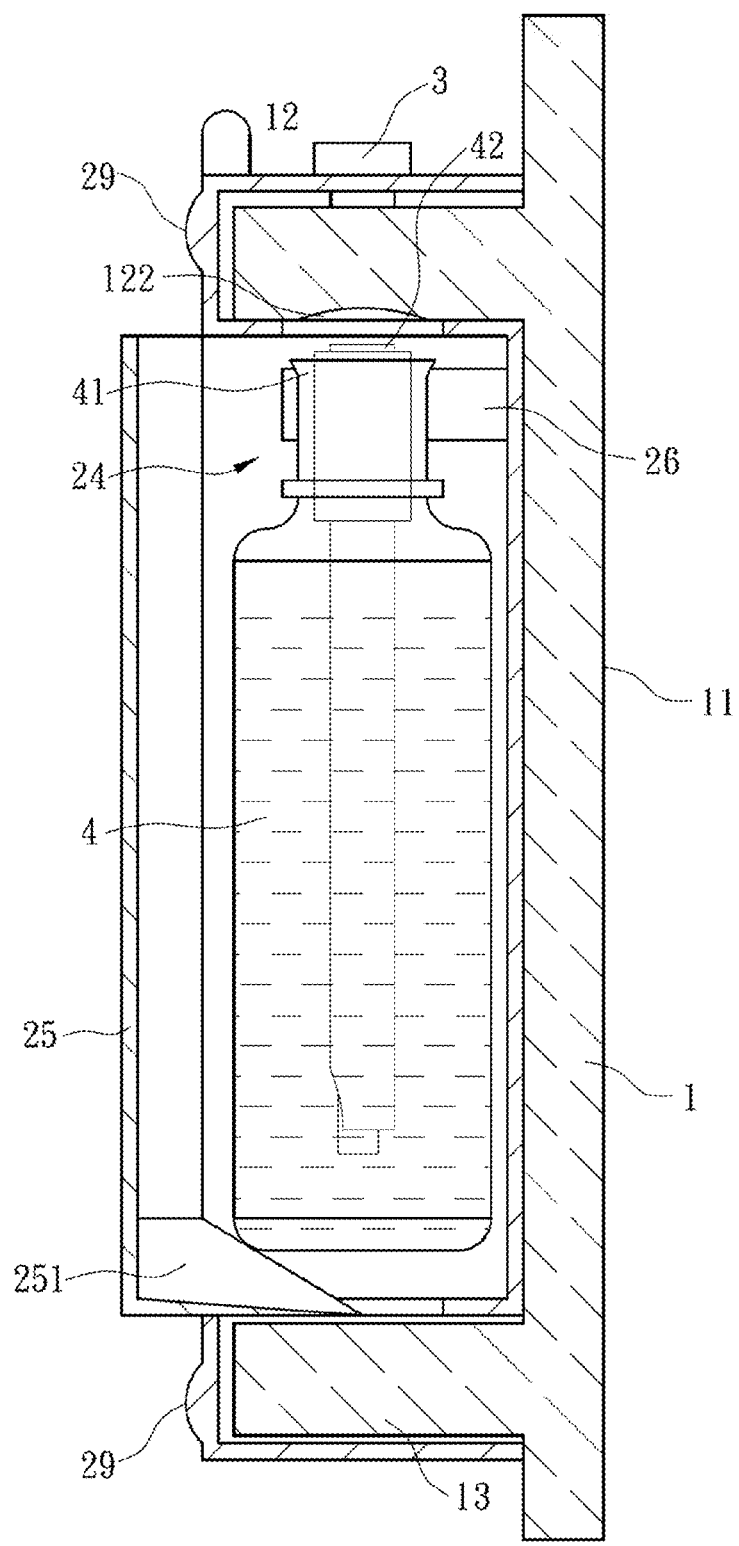
FIG. 5 is a schematic view of a container fixed in a housing of the present invention.
Figure 6:
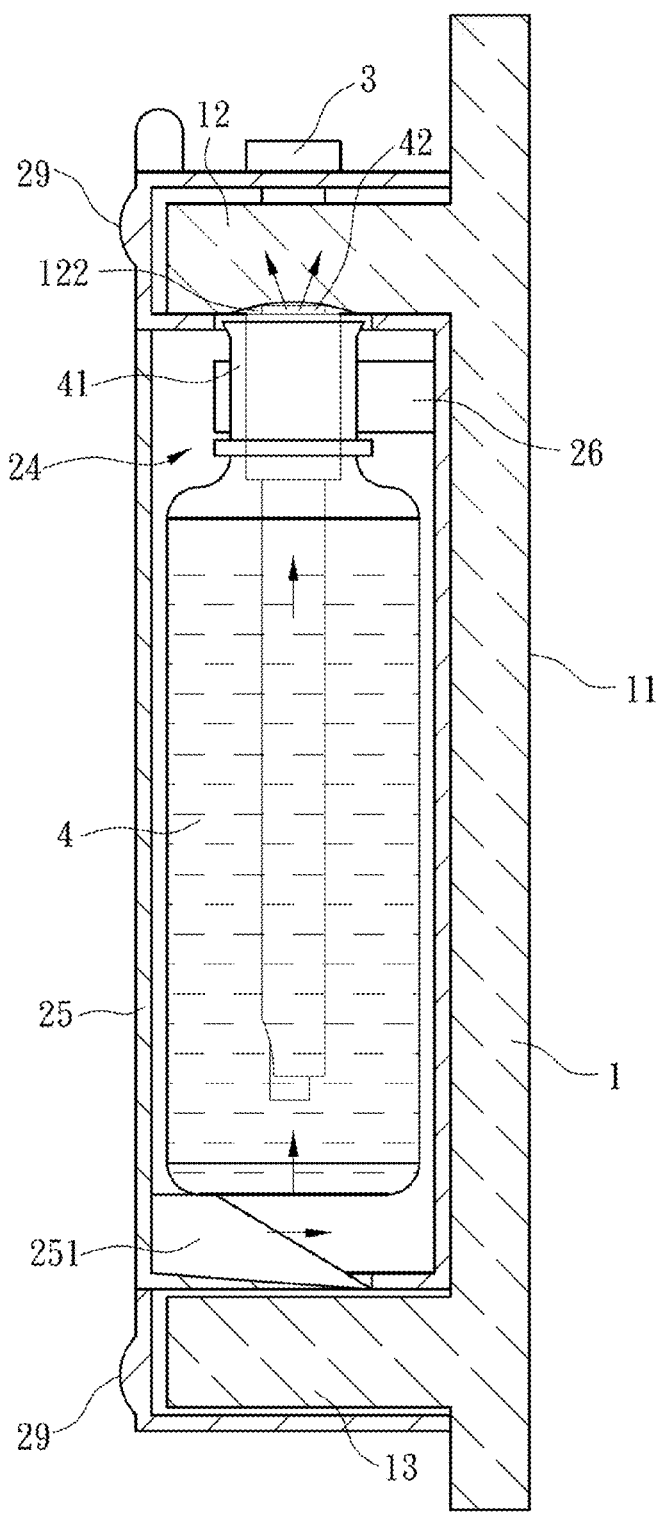
FIG. 6 is a schematic view of a container propped in a housing of the present invention.

An oil wick 42 for absorbing the essential oil is extended from the interior of the container 4 to an anterior end 41 of the container 4, and the oil wick 42 is in contact with one of the two protrusions 12, 13 when the container 4 is propped, such that the essential oil in the container 4 is absorbed by the board 1. In FIG. 5, before the cover 25 is covered onto the space 24, the anterior end 41 of the container 4 is fixed into the space 24 of the housing 2 by the clamp portion 26 as shown in the figure. In FIG. 6, when the cover 25 is covered onto the space 24 the container 4 of this preferred embodiment is propped by the prop portion 251a, and the extended portion of the oil wick 42 is sunken into the recession 122 of the protrusion 12 and contacted with the protrusion 12, so that the essential oil can be absorbed by the board 1 through the protrusion 12, and then vaporized.

In the housing 2 of this preferred embodiment, a plastic strip 29 is installed at top and bottom of the cover 25 for increasing the friction with the wall to prevent the housing 2 from sliding sideway, when the housing 2 abuts the wall.

Figure 7:
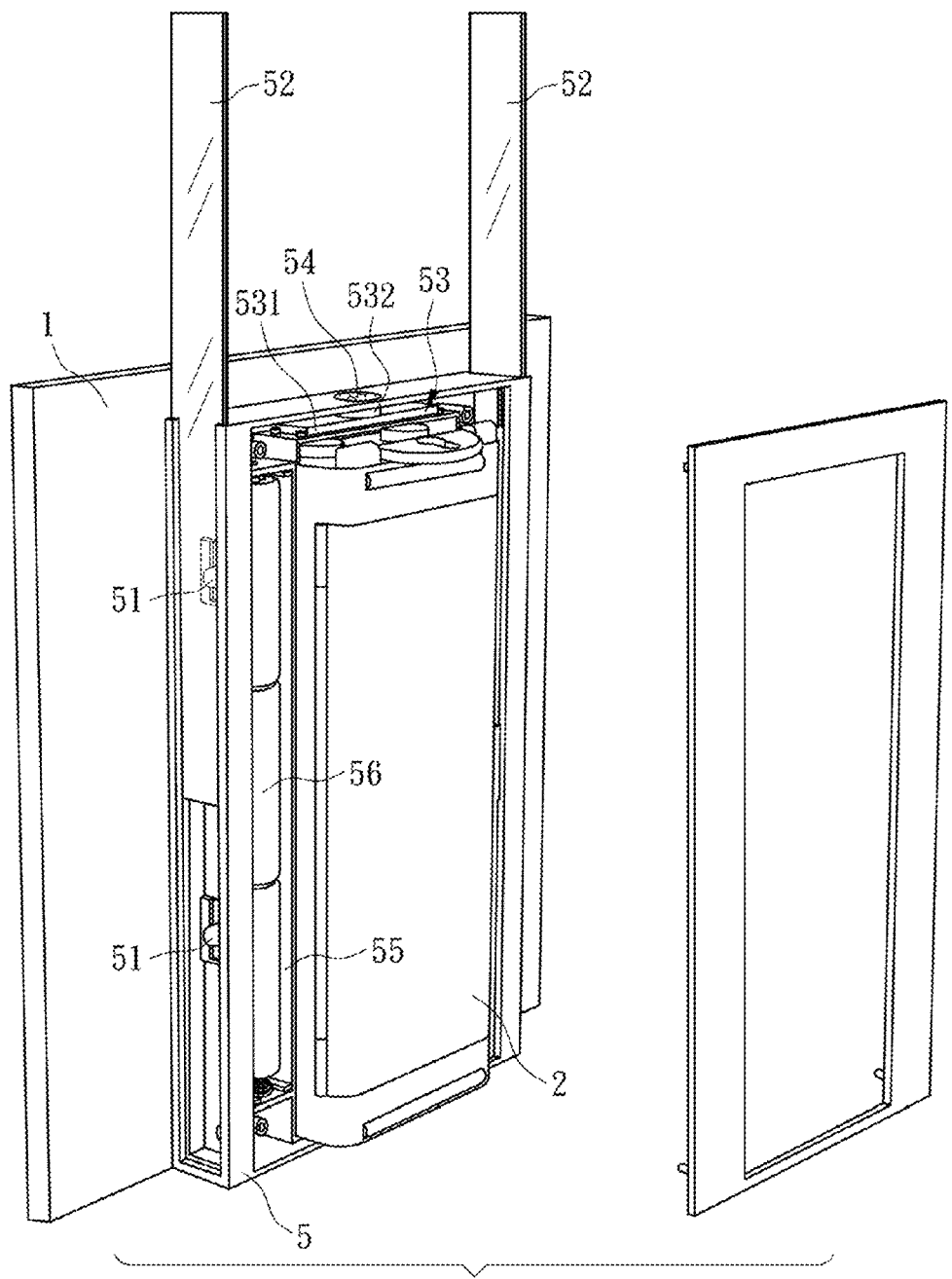
FIG. 7 is a perspective view of a frame of the present invention.

In FIG. 7, a frame 5 is installed at an external periphery of the housing 2, and at least one light emitting element 51 is installed at a side of the frame 5, and a reflective plate 52 is installed at a side of the light emitting element 51 of the frame 5 for increasing a light emitting area, and a switch device 53 is provided for turning on and off the light emitting element 51.

The switch device 53 of this preferred embodiment includes a printed circuit board 531 installed at a gap between the top of the housing 2 and the frame 5 and electrically coupled to a sound control switch 532, and the frame 5 includes a hollow crevice 54 disposed at a position corresponding to the sound control switch 53, such that a sound can be passed through the hollow crevice 54 and received by the sound control switch 532. The frame 5 further includes a battery compartment 55 for installing a battery 56 to supply an electric power to the light emitting element 51. The frame 5 includes two light emitting elements 51 installed on both sides of the frame 5 respectively, wherein the light emitting elements 51 are light emitting diodes.

Figure 2:
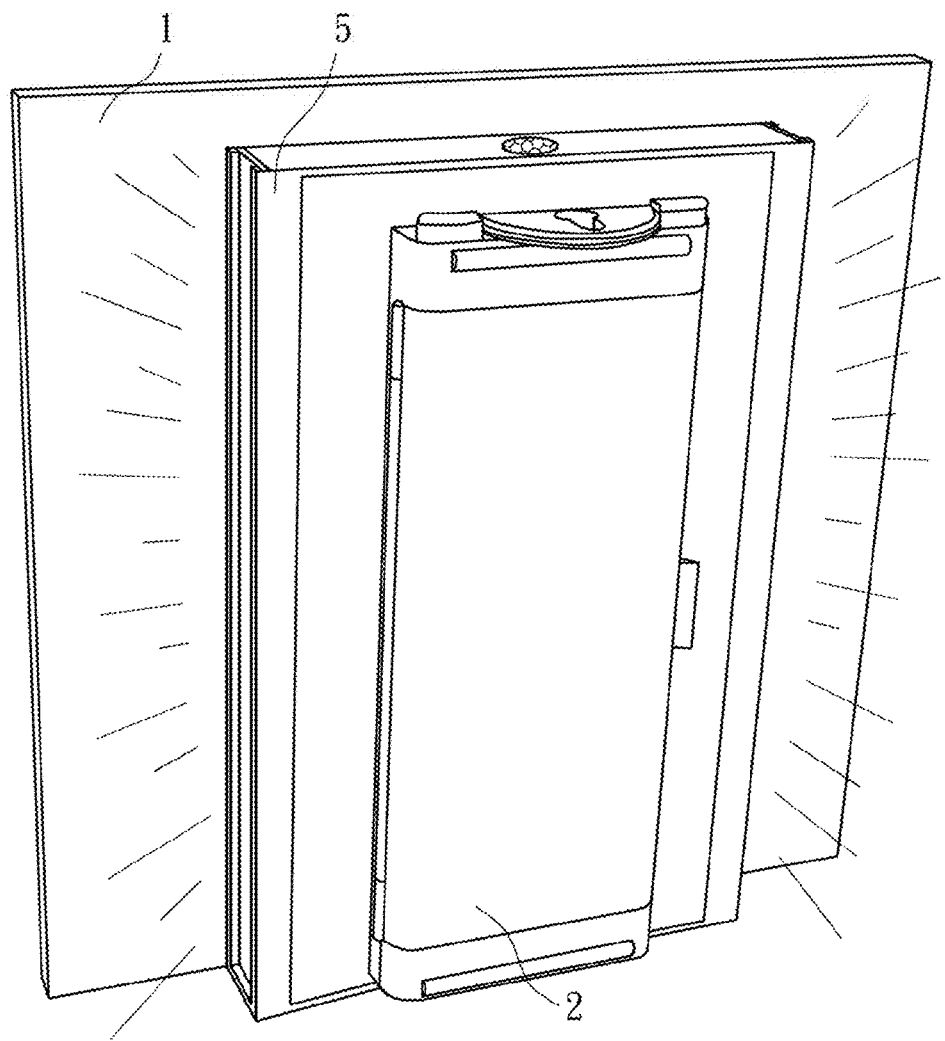
FIG. 2 is a perspective rear view of the present invention.

From the description above, the board 1 of the preferred embodiment absorbs and vaporized the essential oil stored in the container 4 to achieve the effect of producing aromatic air as shown in FIG. 1, and a sound control method is adopted for turning on the light emitting element 51. In addition to the appreciation of the decorative surface 11 with a flower pattern, the light emitting element 51 further provides an amazing optical effect as shown in FIG. 2 as well as an illumination. The aromatic air freshener device of the present invention can be placed on a table instead of being mounted on a wall, and thus the invention provides a flexible way of utilizing space.

In summation of the description above, the present invention has the following advantages. Compared with the first type of air freshener products requiring a fire source for burning and the second type of air freshener products requiring an energy conversion, the aromatic air freshener device of the invention provides a safer way of dispersing aromatic air. Compared with the third type of air freshener products, the invention provides a better optical decorative effect. Therefore, the present invention improves the effects on both aromatic air dispersion and decoration over the prior art.

Of course, there are other embodiments of the present invention with minor modifications, wherein the switch device 53 can be a light control switch for controlling an optical-sensing light emitting control element to be turned on or off, or an infrared switch for remote controlling the light emitting element to be turned on or off, and these different ways of controlling the light emitting control element 51 to be turned on or off brings more fun to the application.

In summation of the description above, the present invention overcomes the shortcomings of the prior art and complies with patent application requirements, and thus is duly applied for patent application, While the invention has been described by means of specific embodiments, numerous modifications and variations could be made thereto by those skilled in the art without departing from the scope and spirit of the invention set forth in the claims.

What is claimed is:

1. A wall-mounted aromatic air freshener device, comprising:
    a board, capable of absorbing and vaporizing an essential oil, and having a decorative surface formed on a front side of the board, and two protrusions disposed on a back side of the board;
    a housing, having two grooves disposed inwardly from a backside of the housing, a hook portion mounted onto a wall, such that the housing is fixed by sheathing the two protrusions into the two grooves respectively, a space formed in the housing for accommodating a container filled with an aromatic essential oil, a cover covered onto this space, a clamp portion disposed in the space of the housing for clamping anterior end of the container, a prop portion disposed at the bottom of the cover and in a covering direction for propping the essential oil container into an oblique surface, an insert slot for receiving the prop portion when the cover is covered onto the space of the housing, and an oil wick extended from the interior of the container to an anterior end of the container for absorbing the essential oil, and contacting one of the two protrusions when the container is propped, such that the essential oil in the container is absorbed by the board; and
    a frame, installed around an external periphery of the housing, and having at least one at least one light emitting element installed at a side of the frame, a reflective plate installed at a side of the at least one light emitting element for increasing a light emitting area, and a switch device for turning on or off the light emitting element.

2. The wall-mounted aromatic air freshener device of claim 1, wherein the switch device includes a printed circuit board electrically coupled to a sound control switch, and the frame includes a hollow gap disposed at a corresponding position of the sound control switch for allowing a sound to be passed to and received by the sound control switch.

3. The wall-mounted aromatic air freshener device of claim 1, wherein the switch device is an optical-sensing light emitting control element provided for turning on or off the at least one light emitting element.

4. The wall-mounted aromatic air freshener device of claim 1, wherein the switch device is an infrared switch used for a remote control of turning on or off the at least one light emitting element.

5. The wall-mounted aromatic air freshener device of claim 1, wherein the frame includes a battery compartment therein for installing a battery to supply electric power to the at least one light emitting element.

6. The wall-mounted aromatic air freshener device of claim 1, wherein the housing includes a plastic strip disposed at the top and bottom of the cover respectively for preventing the housing from sliding sideway when the housing abuts the wall.

7. The wall-mounted aromatic air freshener device of claim 1, wherein the at least one light emitting element is a light emitting diode.

* * * * *